US009604911B2

United States Patent
Briere et al.

(10) Patent No.: US 9,604,911 B2
(45) Date of Patent: Mar. 28, 2017

(54) PROCESS FOR THE SYNTHESIS OF AGOMELATINE

(71) Applicant: LES LABORATOIRES SERVIER, Suresnes (FR)

(72) Inventors: Jean-François Briere, Amfreville-la-mi-Voie (FR); Raphaël Lebeuf, Lille (FR); Vincent Levacher, Fontaine-Sous-Preaux (FR); Christophe Hardouin, Sainte Adresse (FR); Jean-Pierre Lecouve, Le Havre (FR)

(73) Assignee: LES LABORATOIRES SERVIER, Suresnes (FR)

( * ) Notice: Subject to any disclaimer, the term of this patent is extended or adjusted under 35 U.S.C. 154(b) by 0 days.

(21) Appl. No.: 15/100,782

(22) PCT Filed: Dec. 4, 2014

(86) PCT No.: PCT/FR2014/053157
§ 371 (c)(1),
(2) Date: Jun. 1, 2016

(87) PCT Pub. No.: WO2015/082847
PCT Pub. Date: Jun. 11, 2015

(65) Prior Publication Data
US 2016/0368859 A1 Dec. 22, 2016

(30) Foreign Application Priority Data

Dec. 5, 2013 (FR) ...................................... 13 62198

(51) Int. Cl.
| | | |
|---|---|---|
| *C07C 231/12* | (2006.01) | |
| *C07C 303/28* | (2006.01) | |
| *C07C 309/66* | (2006.01) | |
| *C07C 309/73* | (2006.01) | |
| *C07C 231/06* | (2006.01) | |

(52) U.S. Cl.
CPC .......... *C07C 231/12* (2013.01); *C07C 231/06* (2013.01); *C07C 303/28* (2013.01); *C07C 309/66* (2013.01); *C07C 309/73* (2013.01)

(58) Field of Classification Search
CPC ............................ C07C 231/12; C07C 303/28
See application file for complete search history.

(56) References Cited

U.S. PATENT DOCUMENTS

| | | | |
|---|---|---|---|
| 5,194,614 A | 3/1993 | Andrieux | |
| 7,544,839 B2 | 6/2009 | Souvie | |
| 8,143,449 B2 * | 3/2012 | Hardouin | ............... C07C 231/02 564/139 |
| 8,212,077 B2 * | 7/2012 | Hardouin | ............... C07C 231/02 564/219 |
| 8,329,947 B2 | 12/2012 | Bontempelli | |
| 8,653,281 B2 | 2/2014 | Zhang | |

FOREIGN PATENT DOCUMENTS

| | | |
|---|---|---|
| EP | 0447285 | 2/1991 |
| EP | 1564202 | 8/2005 |
| EP | 2151427 | 2/2010 |
| EP | 2322508 | 1/2011 |

OTHER PUBLICATIONS

Li P-K, et al., Bioorganic and Medicinal Chemistry Letters, vol. 7, No. 18, p. 2409-2414, Sep. 23, 1997.
Search Report with Written Opinion for PCT/FR2014/053157 on Feb. 23, 2015.

* cited by examiner

*Primary Examiner* — Golam M Shameem
(74) *Attorney, Agent, or Firm* — Hueschen and Sage

(57) ABSTRACT

Process for the industrial synthesis of the compound of formula (I):

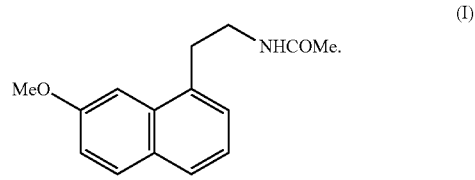

14 Claims, No Drawings

PROCESS FOR THE SYNTHESIS OF AGOMELATINE

The present invention relates to a new process for the industrial synthesis of agomelatine, or N-[2-(7-methoxy-1-naphthyl)ethyl]acetamide, of formula (I):

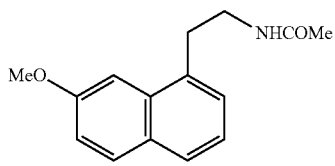

(I)

Agomelatine, or N-[2-(7-methoxy-1-naphthyl)ethyl]acetamide, has valuable pharmacological properties.

It does, in fact, have the double characteristic of being, on the one hand, an agonist of receptors of the melatoninergic system and, on the other hand, an antagonist of the $5\text{-HT}_{2C}$ receptor. These properties provide it with activity in the central nervous system and, more especially, in the treatment of major depression, seasonal affective disorder, sleep disorders, cardiovascular pathologies, pathologies of the digestive system, insomnia and fatigue due to jet-lag, appetite disorders and obesity.

Agomelatine, its preparation and its use in therapeutics have been described in European Patent specifications EP 0 447 285 and EP 1 564 202.

In view of the pharmaceutical value of this compound, it is important to be able to obtain it by an effective industrial synthesis process that is readily transferable to the industrial scale and that results in agomelatine in a good yield and with excellent purity.

Patent specification EP 0 447 285 describes obtaining agomelatine in eight steps starting from 7-methoxy-1-tetralone. In the patent specification EP 1 564 202, the Applicant developed a much more effective and industrialisable synthesis route in only four steps starting from 7-methoxy-1-tetralone making it possible to obtain agomelatine in very reproducible manner in a well-defined crystalline form. However, the search for new synthesis routes, especially starting from starting materials less expensive than 7-methoxy-1-tetralone, is still ongoing.

The Applicant has continued his investigations and has developed a new process for the synthesis of agomelatine starting from 7-methoxy-naphthalen-2-ol: this new starting material has the advantage of being simple and readily obtainable in large amounts at less cost. 7-Methoxy-naphthalen-2-ol also has the advantage of having in its structure a naphthalene ring system, which avoids incorporating an aromatisation step in the synthesis a step which is always problematic from an industrial point of view.

This new process moreover makes it possible to obtain agomelatine in a reproducible manner and without needing laborious purification, with a purity which is compatible with its use as a pharmaceutical active ingredient.

More specifically, the present invention relates to a process for the industrial synthesis of the compound of formula (I):

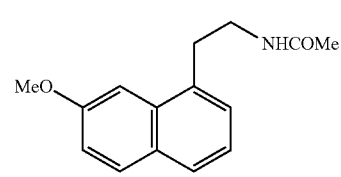

(I)

characterised in that 7-methoxy-naphthalen-2-ol of formula (II):

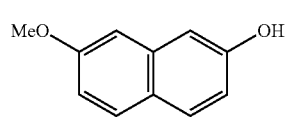

(II)

is used for reaction, the group —$CH_2$—X wherein X represents an —$N(CH_3)_2$, —CO—$N(CH_2\text{-Ph})_2$, —$CH_2$—OH, —CH═$CH_2$ or —CO—$NH_2$ group being introduced at position 1 of the compound of formula (II) to yield the compound of formula (III):

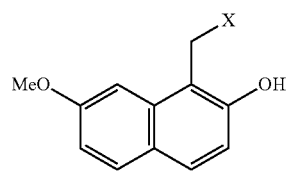

(III)

wherein X represents an —$N(CH_3)_2$, —CO—$N(CH_2\text{-Ph})_2$, —$CH_2$—OH, —CH═$CH_2$ or —CO—$NH_2$ group;

which compound of formula (III) is subjected to a sulphonylation reaction at the aromatic alcohol and the substituent X of which compound of formula (III) is modified, before or after the aromatic alcohol sulphonylation step, by means of customary chemical reactions to yield the compound of formula (IV):

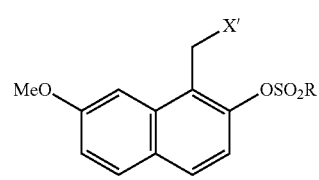

(IV)

wherein X' represents a —CN, —CO—$NH_2$, —$CH_2$—OH, —$CH_2$—$N(CH_2\text{-Ph})_2$, —$CH_2$—NH—CO—$CH_3$, —CH(OH)—$CH_2$—OH, —CHO or (2,5-dioxopyrrolidin-1-yl)methyl group and R represents a —$CH_3$, —$(CH_2)_2$—$CH_3$, —$CF_3$ or tolyl group;

which compound of formula (IV) undergoes a deoxygenation reaction in the presence of a transition metal and a reducing agent to yield:

either, when X' represents the group —$CH_2$—NH—CO—$CH_3$, the compound of formula (I) directly, which is isolated in the form of a solid;

or the compound of formula (V):

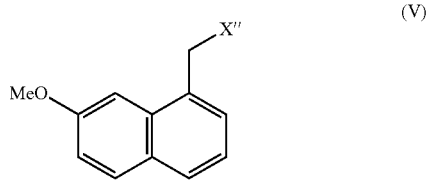

wherein X″ represents a —CN, —CH$_2$—N(CH$_2$-Ph)$_2$, —CH$_2$—OH, —CO—NH$_2$, —CH(OH)—CH$_2$—OH or (2,5-dioxopyrrolidin-1-yl)methyl group;
which compound of formula (V) is then subjected to customary chemical reactions to yield the compound of formula (I), which is isolated in the form of a solid.

A variant of the industrial synthesis process consists of the group X not being modified in the course of conversion of the compound of formula (III) into the compound of formula (IV). The resulting compound, sulphonylated at its aromatic alcohol, then undergoes a deoxygenation reaction by means of the action of a transition metal and a reducing agent. The group X is subsequently modified by means of customary chemical reactions to yield the compound of formula (I), which is isolated in the form of a solid.

The compound of formula (II) is commercially available or readily obtainable by the skilled person using chemical reactions that are customary or described in the literature.

In the process according to the invention, conversion of the compound of formula (II) into the compound of formula (III) wherein X represents the —N(CH$_3$)$_2$ group is accomplished in accordance with the Mannich reaction by means of the action of formaldehyde in the presence of dimethylamine.

In the process according to the invention, conversion of the compound of formula (II) into the compound of formula (III) wherein X represents the —CH$_2$—OH group consists of the compound of formula (II) being subjected to the action of glyoxal (or ethane-1,2-dione) followed by the action of a reducing agent. Advantageously, the reducing agent is lithium aluminium hydride, diisobutylaluminium hydride, lithium triethylborohydride or borane dimethylsulphide. Preferably, the reducing agent is lithium aluminium hydride.

In the process according to the invention, conversion of the compound of formula (II) into the compound of formula (III) wherein X represents the —CO—NH$_2$ or —CO—N(CH$_2$-Ph)$_2$ group is accomplished by means of the action of glyoxal followed by the action, in a heated medium, of the compound of formula NHR'R' wherein R' represents H or a —CH$_2$-Ph group.

Said reaction with glyoxal, which results in the formation of the intermediate lactone of formula (VI):

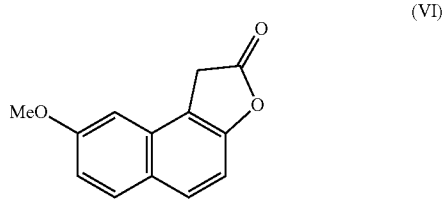 [SMILES: COc1ccc2ccc3c(c2c1)CC(=O)O3]

is preferably carried out in two steps.

In the first step, the compound of formula (II) is dissolved in a basic medium in the presence of glyoxal. The base is preferably sodium hydroxide or potassium hydroxide, and more especially potassium hydroxide.

In the second step, the intermediate product, namely 8-methoxy-1,2-dihydronaphtho[2,1-b]furan-1,2-diol, is directly dissolved in an acid medium, preferably hydrochloric acid, to yield the intermediate lactone of formula (VI).

In the process according to the invention, conversion of the compound of formula (II) into the compound of formula (III) wherein X represents the —CH=CH$_2$ group is accomplished in accordance with the sigmatropic Claisen rearrangement by means of the action of allyl bromide in a basic medium followed by a thermal rearrangement. The action of the allyl bromide is carried out in the presence of a base such as sodium hydride, potassium tert-butoxide, sodium methoxide, potassium hydroxide, sodium hydroxide, potassium carbonate or sodium carbonate. An advantageous embodiment consists of using potassium carbonate as the base in the step comprising reaction with allyl bromide.

In the process according to the invention, conversion of the compound of formula (III) into the compound of formula (IV) consists of a step of sulphonylation of the aromatic alcohol followed by modification of the group X by means of customary chemical reactions, X being as defined hereinbefore. In accordance with another advantageous embodiment, conversion of the compound of formula (III) into the compound of formula (IV) consists of modification of the group X by means of customary chemical reactions followed by a step of sulphonylation of the aromatic alcohol, X being as defined hereinbefore.

Said sulphonylation step is accomplished by means of the action of a sulphonyl chloride, a sulphonic anhydride or a sulphonimide. In accordance with a preferred embodiment, the step of sulphonylation is accomplished by means of the action of tosyl chloride, n-propylsulphonyl chloride, triflic anhydride or phenyl triflimide (or N,N-bis(trifluoro-methylsulphonyl)aniline).

In the process according to the invention, conversion of the compound of formula (IV) into the compound of formula (V) consists of a deoxygenation step in the presence of a transition metal and a reducing agent.

Preferably, the transition metal is nickel, palladium or platinum. The transition metal can be either in the form of a salt or in the form of a simple substance. Preferably, the transition metal salt is a nickel salt or a palladium salt, more preferably a nickel salt.

Advantageously, the reducing agent is either a hydride such as sodium borohydride or lithium aluminium hydride; or an aminoborane such as dimethylamine borane; or an alkoxysilane such as dimethoxymethylsilane; or an alkylsilane such as triethylsilane; or an alkaline earth metal such as magnesium; or dihydrogen.

In accordance with another preferred embodiment, conversion of the compound of formula (IV) into the compound of formula (V) consists of a deoxygenation step in the presence of nickel, especially a nickel salt, and a hydride, preferably sodium borohydride.

In accordance with another preferred embodiment, conversion of the compound of formula (IV) into the compound of formula (V) consists of a deoxygenation step in the presence of palladium and dihydrogen. The dihydrogen is used directly in its gaseous form or is indirectly obtained by decomposition of an ammonium formate.

In accordance with another preferred embodiment, conversion of the compound of formula (IV) into the compound of formula (V) consists of a deoxygenation step in the presence of palladium and an alkaline earth metal, preferably magnesium.

In accordance with another preferred embodiment, conversion of the compound of formula (IV) into the compound of formula (V) consists of a deoxygenation step in the presence of a transition metal, a reducing agent and a ligand. The ligand is preferably a phosphine ligand, and more especially triphenylphosphine.

In accordance with a specific embodiment, the step of deoxygenation of the compound of formula (IV) wherein X' represents the —CH$_2$—NH—CO—CH$_3$ group, which is carried out:
either in the presence of nickel, especially a nickel salt, and a hydride, preferably sodium borohydride;
or in the presence of palladium and dihydrogen;
or in the presence of palladium and an alkaline earth metal;
leads directly to the formation of the compound of formula (I).

This process is especially advantageous for the following reasons:
it makes it possible to obtain the compound of formula (I) on the industrial scale in good yields starting from a simple and low-cost starting material;
it makes it possible to avoid an aromatisation reaction—a step which is always problematic from an industrial point of view—because the naphthalene ring system is present in the starting substrate;
it makes it possible to obtain agomelatine starting from 7-methoxy-naphthalen-2-ol in a reduced number of steps.

The compounds of formulae (III), (IV) and (VI) obtained in accordance with the process of the invention are new and useful as intermediates in the synthesis of agomelatine.

The compounds of formula (V) obtained in accordance with the process of the invention are useful as intermediates in the synthesis of agomelatine. The compounds of formula (V) obtained according to the process of the invention are new, except for (7-methoxynaphthalen-1-yl)acetonitrile, N,N-dibenzyl-2-(7-methoxynaphthalen-1-yl)ethanamine, 2-(7-methoxynaphthalen-1-yl)ethanol and 2-(7-methoxynaphthalen-1-yl)acetamide.

Preferred compounds of formula (III) are the following:
1-[(dimethylamino)methyl]-7-methoxynaphthalen-2-ol;
N,N-dibenzyl-2-(2-hydroxy-7-methoxynaphthalen-1-yl)acetamide;
1-(2-hydroxyethyl)-7-methoxynaphthalen-2-ol;
2-(2-hydroxy-7-methoxynaphthalen-1-yl)acetamide;
7-methoxy-1-(prop-2-en-1-yl)naphthalen-2-ol.

Preferred compounds of formula (IV) are the following:
1-(cyanomethyl)-7-methoxynaphthalen-2-yl trifluoromethanesulphonate;
1-[2-(acetylamino)ethyl]-7-methoxynaphthalen-2-yl 4-methylbenzenesulphonate;
1-[2-(dibenzylamino)ethyl]-7-methoxynaphthalen-2-yl trifluoromethanesulphonate;
1-[2-(acetylamino)ethyl]-7-methoxynaphthalen-2-yl propane-1-sulphonate;
1-[2-(2,5-dioxopyrrolidin-1-yl)ethyl]-7-methoxynaphthalen-2-yl propane-1-sulphonate;
1-(2-hydroxyethyl)-7-methoxynaphthalen-2-yl 4-methylbenzenesulphonate;
1-(2-amino-2-oxoethyl)-7-methoxynaphthalen-2-yl 4-methylbenzenesulphonate;
7-methoxy-1-(2-oxoethyl)naphthalen-2-yl 4-methylbenzenesulphonate;
1-(2,3-dihydroxypropyl)-7-methoxynaphthalen-2-yl 4-methylbenzenesulphonate.

(2-Hydroxy-7-methoxynaphthalen-1-yl)acetonitrile, 7-methoxy-1-(2-{[(4-methylphenyl)-sulphonyl]oxy}ethyl)naphthalen-2-yl 4-methylbenzenesulphonate, 7-methoxy-1-{2-[(propylsulphonyl)oxy]ethyl}naphthalen-2-yl propane-1-sulphonate and 1-[2-(acetylamino)ethyl]-7-methoxynaphthalen-2-yl acetate are new and are useful as intermediates in the synthesis of agomelatine.

The Examples hereinbelow illustrate the invention but do not limit it in any way.

In order to properly validate the reaction routes, the synthesis intermediates were systematically isolated and characterised. However, it is possible to considerably optimise the procedures by limiting the number of intermediates isolated.

The structures of the compounds described were confirmed by the usual spectroscopic techniques: proton NMR (s=singlet; bs=broad singlet; d=doublet; t=triplet; dd=doublet of doublets; m=multiplet); carbon NMR (s=singlet; d=doublet; t=triplet; q=quadruplet); electrospray ionisation mass spectrometry (ESI).

EXAMPLE 1

N-[2-(7-methoxynaphthalen-1-yl)ethyl]acetamide

Step A:
1-[(dimethylamino)methyl]-7-methoxynaphthalen-2-ol

To a solution of 7-methoxy-naphthalen-2-ol (1.74 g; 10 mmol) in ethanol (10 mL) there are added at ambient temperature dimethylamine (40% in water; 1.52 mL; 12 mmol) and then formaldehyde (37% in water; 0.78 mL; 10.5 mmol). After stirring for one hour, the solvent is evaporated off. The crude product obtained (quantitative yield) is used directly in the next Step without further purification.

$^1$H NMR spectroscopic analysis (DMSO-d$_6$, 300.13 MHz, δ in ppm): 11.18 (bs, 1H); 7.68 (d, J=8.8 Hz, 1H); 7.6 (d, J=8.8 Hz, 1H); 7.23 (d, J=2.3 Hz, 1H); 6.93 (dd, J=8.8 and 2.3 Hz, 1H); 6.89 (d, J=8.8 Hz, 1H); 3.96 (s, 2H); 3.86 (s, 3H); 2.3 (s, 6H).

$^{13}$C NMR spectroscopic analysis (DMSO-d$_6$, 75.5 MHz, δ in ppm): 157.7 (s); 156.1 (s); 134.3 (s); 129.9 (d); 128.5 (d); 123.3 (s); 116.0 (d); 114.2 (d); 112.0 (s); 101.6 (d); 55.8 (t); 55.0 (q); 44.3 (2×q).

Step B:
(2-hydroxy-7-methoxynaphthalen-1-yl)acetonitrile

A solution of the product of Step A above (1.155 g; 5 mmol) in dimethylformamide (5 mL) in the presence of potassium cyanide (390 mg; 6 mmol) is heated at 80° C. for 30 hours. After dilution with ethyl acetate, a 2M aqueous solution of HCl (5 mL) is added. The mixture is stirred and then neutralised by addition of dilute NaHCO$_3$ solution. The two phases are separated and the organic fraction is washed three times with brine, dried over sodium sulphate and filtered. Evaporating off the solvent results in a crude product which is then purified by chromatography on a silica gel column (eluant: ether/petroleum ether 40/60) to yield the expected product.

$^1$H NMR spectroscopic analysis (acetone-d$_6$, 300.13 MHz, δ in ppm): 9.25 (bs, 1H, OH); 7.74 (d, J=9.1 Hz, 1H); 7.71 (d, J=8.9 Hz, 1H); 7.31 (d, J=2.5 Hz, 1H); 7.13 (d, J=8.9 Hz, 1H); 7.03 (dd, J=9.1 and 2.5 Hz, 1H); 4.21 (s, 2H); 3.96 (s, 3H).

¹³C NMR spectroscopic analysis (acetone-d₆, 75.5 MHz, δ in ppm): 159.9 (s); 154.1 (s); 135.1 (s); 131.1 (d); 130.4 (d); 124.9 (s); 119.1 (s); 116.2 (d); 115.7 (d); 108.7 (s); 102.1 (d); 55.6 (q); 13.6 (t).

Step C: 1-(cyanomethyl)-7-methoxynaphthalen-2-yl trifluoromethanesulphonate

To a solution of the product of Step B above (120 mg; 0.52 mmol) in dichloromethane (5 mL) there are added N,N-bis(trifluoromethylsulphonyl)aniline (204 mg; 0.571 mmol) and triethylamine (72 µL; 0.52 mmol). After stirring for 16 hours, the solvents are evaporated off and the residue is purified by chromatography on a silica gel column (eluant: ethyl acetate/petroleum ether, gradient from 10/90 to 20/80) to yield the title product (125 mg; 70%).
¹H NMR spectroscopic analysis (CDCl₃, 300.13 MHz, δ in ppm): 7.85-7.78 (m, 2H); 7.3-7.22 (m, 3H); 4.13 (s, 2H); 3.98 (s, 3H).
¹³C NMR spectroscopic analysis (CDCl₃, 75.5 MHz, δ in ppm): 159.9 (s); 145.6 (s); 133.2 (s); 131.2 (d); 130.8 (d); 128.0 (s); 125.0 (s); 120.3 (d); 118.6 (s, J=318 Hz); 116.9 (s); 116.8 (d); 116.0 (s); 102.3 (d); 55.6 (q); 15.2 (t).
Mass spectrometry (ESI: m/z (%): 345 (45) [M]⁺˙; 212 (100); 184 (15); 169 (34); 140 (18).

Step D: (7-methoxynaphthalen-1-yl)acetonitrile

A solution of the product of Step C above (73 mg; 0.212 mmol) in absolute ethanol (4 mL) in the presence of palladium 10% on carbon (4.5 mg; 0.004 mmol) and triethylamine (150 µL) is hydrogenated (4 bars) at ambient temperature for 20 hours. After filtering over Celite, washing with ethyl acetate and evaporating off the solvents, the crude product is purified by chromatography on a silica gel column (eluant: ethyl acetate/petroleum ether 15/85) to yield the title product (28 mg; 67%).
Melting point: 86-87° C.
¹H NMR spectroscopic analysis (CDCl₃, 300.13 MHz, δ in ppm): 7.78 (d, J=8.9 Hz, 1H); 7.77 (d, J=7.8 Hz, 1H); 7.52 (d, J=7.1 Hz, 1H); 7.32 (dd, J=7.8 and 7.1 Hz, 1H); 7.21 (dd, J=8.9 and 2.4 Hz, 1H); 7.03 (d, J=2.4 Hz, 1H); 4.0 (s, 2H); 3.94 (s, 3H).
¹³C NMR spectroscopic analysis (CDCl₃, 75.5 MHz, δ in ppm): 158.5 (s); 132.0 (s); 130.6 (d); 129.1 (s); 128.8 (d); 127.1 (d); 124.4 (s); 123.2 (d); 118.8 (d); 117.7 (s); 101.3 (d); 55.4 (q); 21.9 (t).

Step E: N-[2-(7-methoxynaphthalen-1-yl)ethyl]acetamide 136 g of Raney nickel, 2.06 L of ethanol and 0.23 L of water are introduced into an 8-L reactor. Whilst stirring at 70° C. and under 30 bars of hydrogen, the compound obtained in Step D above (0.8 kg) dissolved in acetic anhydride (2.4 L) is added slowly. When the addition is complete, the reaction mixture is stirred for 1 hour under hydrogen at 30 bars, and then the reactor is depressurised and the liquors are filtered. After concentration of the mixture, the residue is crystallised from a mixture of ethanol/water 35/65 to yield the title product in a yield of 89% and with a chemical purity greater than 99%.
Melting point: 108° C.
¹H NMR spectroscopic analysis (CD₃OD, 300.13 MHz, δ in ppm): 8.21 (bs, 1H); 7.74 (d, J=8.9 Hz, 1H); 7.65 (d, J=8.0 Hz, 1H); 7.52 (d, J=2.5 Hz, 1H); 7.31-7.2 (m, 2H); 7.11 (dd, J=8.9 and 2.5 Hz, 1H); 3.96 (s, 3H); 3.52-3.44 (m, 2H); 3.23-3.18 (m, 2H); 1.94 (s, 3H).
¹³C NMR spectroscopic analysis (CD₃OD, 75.5 MHz, δ in ppm): 173.4 (s); 159.4 (s); 135.1 (s); 134.6 (s); 131.2 (d); 130.8 (s); 128.2 (d); 127.9 (d); 124.2 (d); 119.3 (d); 103.2 (d); 55.9 (q); 41.4 (t); 34.2 (t); 22.6 (q).

EXAMPLE 2

N-[2-(7-methoxynaphthalen-1-yl)ethyl]acetamide

Step A: 1-[(dimethylamino)methyl]-7-methoxynaphthalen-2-yl 4-methylbenzenesulphonate To a solution of the product obtained in Step A of Example 1 (2.042 g; 8.84 mmol) in dimethylformamide (8 mL) there are added potassium tert-butoxide (1.091 g; 9.724 mmol) and then, after 5 minutes, tosyl chloride (1.684 g; 8.84 mmol). After stirring for 6 hours, the solution is diluted with ethyl acetate and washed twice with water and then with brine. The organic phase is dried over sodium sulphate and filtered and the solvent is evaporated off. The crude product obtained is purified by chromatography on a silica gel column (eluant: ethyl acetate/petroleum ether, gradient from 30/70 to 70/30) to yield the expected product in the form of a solid (1.94 g; 57%).
Melting point: 115-118° C.
¹H NMR spectroscopic analysis (CDCl₃, 300.13 MHz, δ in ppm): 7.78 (d, J=8.1 Hz, 2H); 7.7 (d, J=9.0 Hz, 1H); 7.62 (d, J=8.8 Hz, 1H); 7.53 (d, J=2.3 Hz, 1H); 7.34 (d, J=8.1 Hz, 2H); 7.14 (dd, J=9.0 and 2.3 Hz, 1H); 6.96 (d, J=8.8 Hz, 1H); 3.93 (s, 3H); 3.67 (s, 2H); 2.47 (s, 3H); 2.24 (s, 3H).
¹³C NMR spectroscopic analysis (CDCl₃, 75.5 MHz, δ in ppm): 158.4 (s); 146.9 (s); 145.5 (s); 135.1 (s); 133.2 (s); 130.0 (2×d); 129.9 (d); 129.1 (d); 128.6 (2×d); 127.8 (s); 125.7 (s); 118.5 (d); 117.9 (d); 104.5 (d); 55.3 (q); 54.2 (t); 45.6 (2×q); 21.9 (q).

Step B: 1-(cyanomethyl)-7-methoxynaphthalen-2-yl 4-methylbenzenesulphonate

Iodomethane (267 µL; 4.29 mmol) is added to a solution of the product of Step A above (1.5 g; 9.9 mmol) in dimethylformamide (8 mL). After stirring for 4 hours at ambient temperature, potassium cyanide (304 mg; 4.68 mmol) is added. The solution is stirred for 16 more hours and then is diluted with ethyl acetate, washed with water and three times with brine, dried over sodium sulphate and filtered. Evaporating off the solvent yields a crude product which is then purified by chromatography on a silica gel column (eluant: ethyl acetate/petroleum ether 40/60) to yield the expected product (1.276 g; 89%).
¹H NMR spectroscopic analysis (CDCl₃, 300.13 MHz, δ in ppm): 7.77 (d, J=8.3 Hz, 2H); 7.75 (d, J=8.9 Hz, 1H); 7.69 (d, J=8.9 Hz, 1H); 7.35 (d, J=8.3 Hz, 2H); 7.22-7.15 (m, 2H); 7.01 (d, J=8.9 Hz, 1H); 3.98 (s, 2H); 3.95 (s, 3H); 2.45 (s, 3H).

Step C: 1-[2-(acetylamino)ethyl]-7-methoxynaphthalen-2-yl 4-methylbenzenesulphonate The product of Step B above (54 mg; 0.147 mmol), nickel chloride hexahydrate (35 mg; 0.147 mmol), dichloromethane (1.5 mL) and methanol (1.5 mL) are introduced into a sealed flask. Argon is then bubbled into the solution for 5 minutes and then sodium borohydride (100 mg; 2.94 mmol) is added in small portions with caution. After stirring for 30 minutes under argon and at ambient temperature, water is added. After stirring for 15 minutes, the mixture is filtered over Celite and then washed with dichloromethane. The organic fraction is dried over sodium sulphate and then filtered. After evaporating off the solvents, the crude product obtained is placed in the presence of acetic anhydride (1 mL) and sodium acetate (50 mg) with stirring at ambient temperature for 30 minutes. The mixture is poured into a dilute solution of $Na_2CO_3$ and the product is extracted three times with ethyl acetate. The organic fractions are washed with brine, dried over sodium sulphate and filtered. Evaporating off the solvent yields a crude product which is then purified by chromatography on a silica gel column (eluant: ethyl acetate) to yield the expected product in the form of a solid (24 mg; 40%).

$^1$H NMR spectroscopic analysis (CDCl$_3$, 300.13 MHz, δ in ppm): 7.81 (d, J=8.2 Hz, 2H); 7.68 (d, J=8.9 Hz, 1H); 7.62 (d, J=2.4 Hz, 1H); 7.55 (d, J=8.9 Hz, 1H); 7.36 (d, J=8.2 Hz, 2H); 7.14 (dd, J=8.9 and 2.4 Hz, 1H); 6.89 (d, J=8.9 Hz, 1H); 5.97 (m, 1H); 4.01 (s, 3H); 3.53-3.46 (m, 2H); 3.22-3.17 (m, 2H); 2.46 (s, 3H); 1.95 (s, 3H).

$^{13}$C NMR spectroscopic analysis (CDCl$_3$, 75.5 MHz, δ in ppm): 170.9 (s); 158.9 (s); 146.4 (s); 145.7 (s); 134.6 (s); 133.3 (s); 130.1 (2×d); 130.0 (d); 128.5 (2×d); 128.2 (d); 127.7 (s); 126.2 (s); 119.2 (d); 117.8 (d); 103.3 (d); 55.8 (q); 39.4 (t); 26.4 (t); 23.4 (q); 21.9 (q).

Step D:
N-[2-(7-methoxynaphthalen-1-yl)ethyl]acetamide

The product of Step C above (83 mg; 0.2 mmol), nickel chloride (26 mg; 0.2 mmol) and methanol (4 mL) are introduced into a sealed flask. Argon is then bubbled into the solution for 5 minutes and then sodium borohydride (136 mg; 4 mmol) is added in small portions with caution. After stirring for 30 minutes under argon and at ambient temperature, the mixture is filtered over Celite, it is then washed with ethyl acetate and the solvents are evaporated off. The crude product obtained is purified by chromatography on a silica gel column (eluant: ethyl acetate) to yield the expected product (39 mg; 80%).

$^1$H NMR spectroscopic analysis (CD$_3$OD, 300.13 MHz, δ in ppm): 8.21 (bs, 1H); 7.74 (d, J=8.9 Hz, 1H); 7.65 (d, J=8.0 Hz, 1H); 7.52 (d, J=2.5 Hz, 1H); 7.31-7.2 (m, 2H); 7.11 (dd, J=8.9 and 2.5 Hz, 1H); 3.96 (s, 3H); 3.52-3.44 (m, 2H); 3.23-3.18 (m, 2H); 1.94 (s, 3H).

$^{13}$C NMR spectroscopic analysis (CD$_3$OD, 75.5 MHz, δ in ppm): 173.4 (s); 159.4 (s); 135.1 (s); 134.6 (s); 131.2 (d); 130.8 (s); 128.2 (d); 127.9 (d); 124.2 (d); 119.3 (d); 103.2 (d); 55.9 (q); 41.4 (t); 34.2 (t); 22.6 (q).

EXAMPLE 3

N-[2-(7-methoxynaphthalen-1-yl)ethyl]acetamide

Step A: 8-methoxynaphtho[2,1-b]furan-2(1H)-one

An aqueous solution of 85% potassium hydroxide (2.76 g; 40 mmol) and 7-methoxy-naphthalen-2-ol (6.96 g; 40 mmol) in water (80 mL) is added dropwise at ambient temperature to a solution of glyoxal (40% in water; 28 mL; 240 mmol). After stirring for 3 hours, the white precipitate is collected by filtration and washed with water. The solid obtained (8-methoxy-1,2-dihydronaphtho[2,1-b]furan-1,2-diol) is dissolved in 1,2-dichloroethane (160 mL) and aqueous 3M HCl solution (300 mL) is then added. The heterogeneous mixture is heated at 50° C. with vigorous stirring. After 1.5 hours, all the solid is dissolved and the two phases are separated. The organic phase is collected and the solvents evaporated off. The crude product is dried by azeotropic distillation with toluene to yield the title product (8.69 g) which will be used directly in the next Step without further purification.

$^1$H NMR spectroscopic analysis (DMSO-d$_6$, 300.13 MHz, δ in ppm): 7.88 (d, J=8.8 Hz, 1H); 7.85 (d, J=8.6 Hz, 1H); 7.28 (d, J=8.8 Hz, 1H); 7.12-7.06 (m, 2H); 4.15 (s, 2H); 3.89 (s, 3H).

Step B: N,N-dibenzyl-2-(2-hydroxy-7-methoxynaphthalen-1-yl)acetamide

The product of Step A above (1.976 g; 9.23 mmol) and dibenzylamine (4 mL; 20.3 mmol) are introduced into a flask and then heated at 120° C. for 2 hours. After cooling, the residue is diluted with ethyl acetate (200 mL). Adding aqueous 2M HCl solution precipitates the dibenzylamine hydrochloride salt, which is then filtered off over Celite. The organic phase is washed with aqueous 2M HCl solution, then washed with brine, dried over sodium sulphate and filtered. After evaporating off the solvents, the crude product obtained is purified by chromatography on a silica gel column (eluant: ethyl acetate/petroleum ether 30/70) to yield the expected product in the form of a solid (2.88 g; 76%).

Melting point: 155-157° C.

$^1$H NMR spectroscopic analysis (CDCl$_3$, 300.13 MHz, δ in ppm): 9.85 (bs, 1H); 7.66 (d, J=8.7 Hz, 1H); 7.62 (d, J=8.7 Hz, 1H); 7.4-7.24 (m, 6H); 7.18-7.14 (m, 4H); 7.08 (d, J=8.7 Hz, 1H); 6.95-6.91 (m, 2H); 4.72 (s, 2H); 4.64 (s, 2H); 4.21 (s, 2H); 3.55 (s, 3H).

$^{13}$C NMR spectroscopic analysis (CDCl$_3$, 75.5 MHz, δ in ppm): 174.6 (s); 158.6 (s); 155.8 (s); 136.4 (s); 135.5 (s); 134.1 (s); 130.6 (d); 129.3 (d); 129.2 (2×d); 128.9 (2×d); 128.4 (2×d); 128.1 (d); 127.8 (d); 126.4 (2×d); 124.6 (s); 117.5 (d); 114.9 (d); 111.5 (s); 101.2 (d); 55.9 (q); 50.8 (t); 49.0 (t); 31.5 (t).

Step C: 1-[2-(dibenzylamino)ethyl]-7-methoxynaphthalen-2-ol

A 1M solution of borane-tetrahydrofuran complex in tetrahydrofuran (1.7 mL; 1.7 mmol) is added to a solution of the product of Step B above (230 mg; 0.56 mmol) in tetrahydrofuran (10 mL). The mixture is heated at reflux for 2 hours, and aqueous 2M HCl solution (10 mL) is then added. After stirring overnight, saturated NaHCO$_3$ solution is added to achieve a neutral pH and the product is extracted three times with ethyl acetate. The organic fractions are dried over sodium sulphate and filtered and the solvent is evaporated off. The crude product obtained is purified by chromatography on a silica gel column (eluant: ethyl acetate/petroleum ether 30/70) to yield the expected product (150 mg; 72%).

$^1$H NMR spectroscopic analysis (CDCl$_3$, 300.13 MHz, δ in ppm): 12.09 (bs, 1H); 7.69 (d, J=8.9 Hz, 1H); 7.61 (d, J=8.8 Hz, 1H); 7.44-7.26 (m, 10H); 7.14 (d, J=8.8 Hz, 1H); 7.12 (d, J=2.4 Hz, 1H); 7.0 (dd, J=8.8 and 2.4 Hz, 1H); 3.93 (s, 3H); 3.79 (s, 4H); 3.21-3.18 (m, 2H); 3.01-2.98 (m, 2H).

Step D: 1-[2-(dibenzylamino)ethyl]-7-methoxynaphthalen-2-yl trifluoromethanesulphonate Triflic anhydride (135 μL; 0.801 mmol) is added at 0° C. to a solution of the product of Step C above (303 mg; 0.763 mmol) in dichloromethane (10 mL). After stirring for 2 hours at that temperature, the solvent is evaporated off. The residue is taken up in a mixture of diethyl ether/aqueous semi-saturated NaHCO$_3$ solution. After separation, the organic phase is dried over sodium sulphate and filtered. After evaporating off the solvents, the crude product obtained is purified by chromatography on a silica gel column (eluant: ethyl acetate/petroleum ether 10/90) to yield the expected product (306 mg; 76%).

$^1$H NMR spectroscopic analysis (CDCl$_3$, 300.13 MHz, δ in ppm): 7.73 (d, J=8.9 Hz, 1H); 7.69 (d, J=8.9 Hz, 1H); 7.44-7.4 (m, 4H); 7.35-7.22 (m, 7H); 7.15 (dd, J=8.9 and 2.3 Hz, 1H); 6.99 (d, J=2.3 Hz, 1H); 3.78 (s, 4H); 3.6 (s, 3H); 3.43-3.37 (m, 2H); 2.91-2.86 (m, 2H).

$^{13}$C NMR spectroscopic analysis (CDCl$_3$, 75.5 MHz, δ in ppm): 158.9 (s); 146.1 (s); 139.8 (2×s); 134.3 (s); 130.3 (d); 128.7 (4×d); 128.6 (d); 128.3 (4×d); 128.1 (s); 127.4 (s); 127.0 (2×d); 119.5 (d); 118.7 (s, J$_{C-F}$=318 Hz); 116.8 (d); 102.8 (d); 58.3 (2×t); 55.3 (q); 52.5 (t); 24.6 (t).

Step E: N,N-dibenzyl-2-(7-methoxynaphthalen-1-yl)ethanamine

The product of Step D above (130 mg; 0.25 mmol), palladium acetate (5.6 mg; 0.025 mmol), triphenylphosphine (20 mg; 0.075 mmol), ammonium formate (142 mg; 2.25 mmol) and dimethylformamide (1 mL) are introduced into a flask. After stirring for 16 hours at 60° C., the solution is diluted with ethyl acetate, washed with water, washed twice with brine, dried over sodium sulphate and filtered. After evaporating off the solvents, the crude product obtained is purified by chromatography on a silica gel column (eluant: ethyl acetate/petroleum ether 10/90) to yield the title product in the form of a white solid (93 mg; 98%).

Melting point: 92-93° C.

$^1$H NMR spectroscopic analysis (CDCl$_3$, 300.13 MHz, δ in ppm): 7.74 (d, J=8.9 Hz, 1H); 7.65 (m, 1H); 7.43-7.39 (m, 4H); 7.35-7.22 (m, 8H); 7.11 (dd, J=8.9 and 2.4 Hz, 1H); 7.05 (d, J=2.4 Hz, 1H); 3.76 (s, 4H); 3.67 (s, 3H); 3.29-3.23 (m, 2H); 2.92-2.86 (m, 2H).

$^{13}$C NMR spectroscopic analysis (CDCl$_3$, 75.5 MHz, δ in ppm): 157.6 (s); 139.9 (2×s); 135.3 (s); 133.2 (s); 130.3 (d); 129.3 (s); 128.7 (4×d); 128.3 (4×d); 127.3 (d); 127.0 (2×d); 126.5 (d); 123.3 (d); 118.2 (d); 102.2 (d); 58.6 (2 t); 55.2 (q); 54.2 (t); 31.5 (t).

Step F: N-[2-(7-methoxynaphthalen-1-yl)ethyl]acetamide

The product of Step E above (66 mg; 0.173 mmol), palladium hydroxide on carbon (20% Pd, 60% moisture; 10 mg), ethanol (2 mL) and ethyl acetate (2 mL) are introduced into a flask placed in an autoclave. The autoclave is filled with pressurised hydrogen (5 bars) and the mixture is stirred for 30 hours. The solution is then filtered over Celite and washed with ethanol and the solvents are evaporated off. Acetic anhydride (500 μL) and sodium acetate (100 mg) are added to the crude reaction product. After stirring for 4 hours, the mixture is diluted with ethyl acetate. The organic phase is washed twice with aqueous 2M sodium hydroxide solution and with brine, dried over sodium sulphate and filtered. After evaporating off the solvents, the expected product is obtained in the pure state (41 mg; 98%).

$^1$H NMR spectroscopic analysis (CD$_3$OD, 300.13 MHz, δ in ppm): 8.21 (bs, 1H); 7.74 (d, J=8.9 Hz, 1H); 7.65 (d, J=8.0 Hz, 1H); 7.52 (d, J=2.5 Hz, 1H); 7.31-7.2 (m, 2H); 7.11 (dd, J=8.9 and 2.5 Hz, 1H); 3.96 (s, 3H); 3.52-3.44 (m, 2H); 3.23-3.18 (m, 2H); 1.94 (s, 3H).

$^{13}$C NMR spectroscopic analysis (CD$_3$OD, 75.5 MHz, δ in ppm): 173.4 (s); 159.4 (s); 135.1 (s); 134.6 (s); 131.2 (d); 130.8 (s); 128.2 (d); 127.9 (d); 124.2 (d); 119.3 (d); 103.2 (d); 55.9 (q); 41.4 (t); 34.2 (t); 22.6 (q).

EXAMPLE 4

N-[2-(7-methoxynaphthalen-1-yl)ethyl]acetamide

Step A: 1-(2-hydroxyethyl)-7-methoxynaphthalen-2-ol

The product obtained in Step A of Example 3 (8.96 g; 40 mmol) is dissolved in tetrahydrofuran (160 mL), and then lithium aluminium hydride (1.52; 40 mmol) is added in portions at 0° C. under nitrogen flow. The mixture is stirred for 16 hours at ambient temperature and the reaction is then stopped at 0° C. with addition of ethyl acetate and then water. Aqueous 1M sulphuric acid solution (80 mL) is added. After stirring for one hour, the heterogeneous mixture is filtered over Celite and washed with ethyl acetate. After decanting and separating, the organic phase is washed with water and then with brine. The solution is again filtered through a thin layer of silica and the solvents are evaporated off to yield the title product without further purification (8.21 g; 94% starting from 7-methoxy-naphthalen-2-ol).

$^1$H NMR spectroscopic analysis (DMSO-d$_6$, 300.13 MHz, δ in ppm): 7.6 (d, J=8.8 Hz, 1H); 7.49 (d, J=8.8 Hz, 1H); 7.25 (d, J=2.4 Hz, 1H); 6.94 (d, J=8.8 Hz, 1H); 6.9 (dd, J=8.8 and 2.4 Hz, 1H); 3.9 (s, 3H); 3.79-3.73 (m, 2H); 3.31-3.25 (m, 2H).

Step B: 7-methoxy-1-(2-{[(4-methylphenyl)sulphonyl]oxy}ethyl)naphthalen-2-yl 4-methylbenzenesulphonate The product of Step A above (436 mg; 2 mmol), dichloromethane (10 mL), triethylamine (670 μL; 4.8 mmol) and 4-dimethylaminopyridine (12 mg; 0.1 mmol) are introduced into a flask. After cooling to 0° C., tosyl chloride (800 mg; 4 mmol) is added all at once and the solution is stirred for 2 hours at 0° C. and then for 14 hours at ambient temperature. After evaporating off the solvent, the residue is taken up in ethyl acetate and water. The organic fraction is washed with water and with brine, dried over sodium sulphate and filtered. After evaporating off the solvent, the crude product obtained is purified by chromatography on a silica gel column (eluant: ethyl acetate/petroleum ether, gradient from 20/80 to 30/70) to yield the title product (728 mg; 69%).

$^1$H NMR spectroscopic analysis (CDCl$_3$, 300.13 MHz, δ in ppm): 7.78 (d, J=8.3 Hz, 2H); 7.69 (d, J=9.1 Hz, 1H); 7.66 (d, J=8.3 Hz, 2H); 7.59 (d, J=8.9 Hz, 1H); 7.35 (d, J=8.3 Hz, 2H); 7.26 (d, J=2.4 Hz, 1H); 7.23 (d, J=8.3 Hz, 2H); 7.15 (dd, J=8.9 and 2.4 Hz, 1H); 7.03 (d, J=9.1 Hz, 1H); 4.2 (t, J=7.7 Hz, 2H); 3.94 (s, 3H); 3.34 (d, J=7.7 Hz, 2H); 2.47 (s, 3H); 2.39 (s, 3H).

Step C: 1-[2-(acetylamino)ethyl]-7-methoxynaphthalen-2-yl 4-methylbenzenesulphonate The product of Step B above (124 mg; 0.236 mmol), acetonitrile (1 mL) and 35% aqueous ammonia solution (1 mL) are introduced into a sealed flask. The flask is placed in a bath heated at 110° C. and the solution is stirred for 3.5 hours. After cooling, the solution is diluted with ethyl acetate, washed with dilute NaHCO$_3$ solution, washed with brine, dried over sodium sulphate and filtered. After evaporating off the solvents, the crude product is dissolved in acetic anhydride (1 mL), and sodium acetate (300 mg) is then added. After stirring for 14 hours, the mixture is poured into dilute NaHCO$_3$ solution. After stirring for 30 minutes, the product is extracted three times with ethyl acetate. The organic phase is washed with water and with brine, dried over sodium sulphate and filtered. After evaporating off the solvents, the crude product is purified by chromatography on a silica gel column (eluant: ethyl acetate) to yield the title product (84 mg; 86%).

$^1$H NMR spectroscopic analysis (CDCl$_3$, 300.13 MHz, δ in ppm): 7.81 (d, J=8.2 Hz, 2H); 7.68 (d, J=8.9 Hz, 1H); 7.62 (d, J=2.4 Hz, 1H); 7.55 (d, J=8.9 Hz, 1H); 7.36 (d, J=8.2 Hz, 2H); 7.14 (dd, J=8.9 and 2.4 Hz, 1H); 6.89 (d, 8.9 Hz, 1H); 5.97 (m, 1H); 4.01 (s, 3H); 3.53-3.46 (m, 2H); 3.22-3.17 (m, 2H); 2.46 (s, 3H); 1.95 (s, 3H).

$^{13}$C NMR spectroscopic analysis (CDCl$_3$, 75.5 MHz, δ in ppm): 170.9 (s); 158.9 (s); 146.4 (s); 145.7 (s); 134.6 (s); 133.3 (s); 130.1 (2×d); 130.0 (d); 128.5 (2×d); 128.2 (d); 127.7 (s); 126.2 (s); 119.2 (d); 117.8 (d); 103.3 (d); 55.8 (q); 39.4 (t); 26.4 (t); 23.4 (q); 21.9 (q).

Step D:
N-[2-(7-methoxynaphthalen-1-yl)ethyl]acetamide

The title product is obtained according to the process described in Step D of Example 2, using the product of Step C above as starting reagent.

$^1$H NMR spectroscopic analysis (CD$_3$OD, 300.13 MHz, δ in ppm): 8.21 (bs, 1H); 7.74 (d, J=8.9 Hz, 1H); 7.65 (d, J=8.0 Hz, 1H); 7.52 (d, J=2.5 Hz, 1H); 7.31-7.20 (m, 2H); 7.11 (dd, J=8.9 and 2.5 Hz, 1H); 3.96 (s, 3H); 3.52-3.44 (m, 2H); 3.23-3.18 (m, 2H); 1.94 (s, 3H).

$^{13}$C NMR spectroscopic analysis (CD$_3$OD, 75.5 MHz, δ in ppm): 173.4 (s); 159.4 (s); 135.1 (s); 134.6 (s); 131.2 (d); 130.8 (s); 128.2 (d); 127.9 (d); 124.2 (d); 119.3 (d); 103.2 (d); 55.9 (q); 41.4 (t); 34.2 (t); 22.6 (q).

EXAMPLE 5

N-[2-(7-methoxynaphthalen-1-yl)ethyl]acetamide

Step A: 7-methoxy-1-{2-[(propylsulphonyl)oxy]ethyl}naphthalen-2-yl propane-1-sulphonate The product obtained in Step A of Example 4 (2.45 g; 11.238 mmol) is dissolved in dichloromethane (60 mL), and triethylamine (3.7 mL; 26.4 mmol) is then added. After cooling to 0° C., n-propylsulphonyl chloride (2.8 mL; 24.6 mmol) is added dropwise. After stirring for 2 hours at ambient temperature, the solvent is evaporated off. The residue obtained is taken up in diethyl ether and water. After separation, the organic phase is washed with dilute aqueous HCl solution, with water and with brine, dried over sodium sulphate and filtered. After evaporating off the solvent, the crude product obtained is purified by chromatography on a silica gel column (eluant: ethyl acetate/petroleum ether 20/80) to yield the title product in the form of a solid (3.335 g; 66% over 3 steps starting from 7-methoxy-naphthalen-2-ol).

$^1$H NMR spectroscopic analysis (CDCl$_3$, 300.13 MHz, δ in ppm): 7.72 (m, 2H); 7.37 (d, J=2.4 Hz, 1H); 7.31 (d, J=9.0 Hz, 1H); 7.17 (dd, J=9.0 and 2.4 Hz, 1H); 4.48 (t, J=8.0 Hz, 2H); 3.96 (s, 3H); 3.6 (t, J=8.0 Hz, 2H); 3.45-3.4 (m, 2H); 3.04-2.98 (m, 2H); 2.1 (m, 2H); 1.8 (m, 2H); 1.17 (t, J=7.3 Hz, 3H); 0.99 (t, J=7.3 Hz, 3H).

Step B:
1-[2-(acetylamino)ethyl]-7-methoxynaphthalen-2-yl propane-1-sulphonate

The product of Step A above (532 mg; 1.237 mmol), acetonitrile (18 mL) and aqueous 35% ammonia solution (18 mL) are introduced into a sealed flask. The mixture is then placed in a bath heated at 110° C. for 3 hours. The solvents are then evaporated off under reduced pressure, carrying out azeotropic distillation with ethanol. The crude product is dissolved in acetic anhydride (5 mL) and, afterwards, sodium acetate (500 mg) is added. After stirring for one hour, the solution is diluted with ethyl acetate and is then poured with caution into saturated aqueous NaHCO$_3$ solution. After stirring for 15 minutes, the two phases are separated and the aqueous phase is extracted twice with ethyl acetate. The organic fractions are combined, washed with water and then with brine, dried over sodium sulphate and filtered. After evaporating off the solvent, the crude product obtained is purified by chromatography on a silica gel column (eluant: ethyl acetate) to yield the title product (289 mg; 64%).

$^1$H NMR spectroscopic analysis (CDCl$_3$, 300.13 MHz, δ in ppm): 7.73 (d, J=8.9 Hz, 1H); 7.68 (d, J=8.9 Hz, 1H); 7.62 (d, J=2.5 Hz, 1H); 7.27 (d, J=8.9 Hz, 1H); 7.16 (dd, J=8.9 and 2.5 Hz, 1H); 5.95 (m, 1H); 4.02 (s, 3H); 3.62-3.54 (m, 2H); 3.43-3.32 (m, 2H); 2.09 (m, 2H); 1.17 (t, J=7.4 Hz, 3H).

$^{13}$C NMR spectroscopic analysis (CDCl$_3$, 75.5 MHz, δ in ppm): 170.9 (s); 159.0 (s); 145.6 (s); 134.7 (s); 130.2 (d); 128.6 (d); 127.7 (s); 126.0 (s); 119.2 (d); 118.1 (d); 103.3 (d); 55.9 (q); 53.6 (t); 39.4 (t); 26.5 (t); 23.4 (q); 17.6 (t); 13.1 (q).

Step C:
N-[2-(7-methoxynaphthalen-1-yl)ethyl]acetamide

The product of Step B above (327 mg; 0.896 mmol), ammonium acetate (1.19 g; 15.54 mmol), palladium 10% on carbon (95 mg; 0.09 mmol), ethanol (3 mL) and powdered magnesium (83 mg; 3.584 mmol) are introduced into a flask. After stirring for 16 hours, the heterogeneous mixture is filtered over Celite and washed with ethyl acetate. After evaporating off the solvents, the crude product obtained is purified by chromatography on a silica gel column (eluant: ethyl acetate) to yield the title product (190 mg; 87%).

$^1$H NMR spectroscopic analysis (CD$_3$OD, 300.13 MHz, δ in ppm): 8.21 (bs, 1H); 7.74 (d, J=8.9 Hz, 1H); 7.65 (d, J=8.0 Hz, 1H); 7.52 (d, J=2.5 Hz, 1H); 7.31-7.2 (m, 2H); 7.11 (dd, J=8.9 and 2.5 Hz, 1H); 3.96 (s, 3H); 3.52-3.44 (m, 2H); 3.23-3.18 (m, 2H); 1.94 (s, 3H).

$^{13}$C NMR spectroscopic analysis (CD$_3$OD, 75.5 MHz, δ in ppm): 173.4 (s); 159.4 (s); 135.1 (s); 134.6 (s); 131.2 (d); 130.8 (s); 128.2 (d); 127.9 (d); 124.2 (d); 119.3 (d); 103.2 (d); 55.9 (q); 41.4 (t); 34.2 (t); 22.6 (q).

EXAMPLE 6

N-[2-(7-methoxynaphthalen-1-yl)ethyl]acetamide

Step A: 1-[2-(2, 5-dioxopyrrolidin-1-yl)ethyl]-7-methoxynaphthalen-2-yl propane-1-sulphonate The product obtained in Step A of Example 5 (240 mg; 0.558 mmol), potassium carbonate (231 mg; 1.674 mmol), succinimide (66 mg; 0.67 mmol) and dimethylformamide (2 mL) are introduced into a flask. After stirring for 16 hours at 100° C., the solution is diluted with ethyl acetate, washed with dilute aqueous HCl solution, with water and with brine and then dried over sodium sulphate and filtered. After evaporating off the solvent, the crude product obtained is purified by chromatography on a silica gel column (eluant: ethyl acetate/petroleum ether 70/30) to yield the title product (123 mg; 57%).

$^1$H NMR spectroscopic analysis (CDCl$_3$, 300.13 MHz, δ in ppm): 7.74 (d, J=9.0 Hz, 1H); 7.7 (d, J=8.9 Hz, 1H); 7.6 (d, J=2.4 Hz, 1H); 7.38 (d, J=9.0 Hz, 1H); 7.16 (dd, J=8.9 and 2.4 Hz, 1H); 4.05 (s, 3H); 3.86-3.8 (m, 2H); 3.58-3.52 (m, 2H); 3.33-3.27 (m, 2H); 2.72 (s, 4H); 2.14 (m, 2H); 1.2 (t, J=7.5 Hz, 3H).

$^{13}$C NMR spectroscopic analysis (CDCl$_3$, 75.5 MHz, δ in ppm): 177.3 (2×s); 159.1 (s); 145.3 (s); 134.4 (s); 130.4 (d); 128.8 (d); 127.7 (s); 124.2 (s); 119.2 (d); 118.4 (d); 102.4 (d); 55.8 (q); 53.5 (t); 37.7 (t); 28.4 (2×t); 24.7 (t); 17.5 (t); 13.1 (q).

Step B:
N-[2-(7-methoxynaphthalen-1-yl)ethyl]acetamide

The product of Step A above (65 mg; 0.16 mmol), ammonium acetate (240 mg; 3.12 mmol), palladium 10% on carbon (16.5 mg; 0.016 mmol), methanol (0.7 mL) and powdered magnesium (8 mg; 0.36 mmol) in a single portion are introduced into a flask. After stirring for 12 hours at 30° C., the heterogeneous mixture is filtered over Celite and then washed with ethyl acetate. After evaporating off the solvents, the crude product is dissolved in ethanol (2 mL) in a sealed tube and then aqueous sodium hydroxide solution (180 mg; 4.5 mmol in 1 mL of water) is added. The mixture is then diluted with acetic anhydride (5 mL), and sodium acetate (500 mg) is introduced. After stirring for one hour, the solution is diluted with ethyl acetate and then poured with caution into saturated aqueous NaHCO$_3$ solution. After stirring for 15 minutes, the two phases are separated and the aqueous phase is extracted twice with ethyl acetate. The organic fractions are combined, washed with water and with brine, dried over sodium sulphate and filtered. After the solvent has been evaporated off, the crude product obtained is purified by chromatography on a silica gel column (eluant: ethyl acetate) to yield the title product (14.4 mg; 37%).

$^1$H NMR spectroscopic analysis (CD$_3$OD, 300.13 MHz, δ in ppm): 8.21 (bs, 1H); 7.74 (d, J=8.9 Hz, 1H); 7.65 (d, J=8.0 Hz, 1H); 7.52 (d, J=2.5 Hz, 1H); 7.31-7.2 (m, 2H); 7.11 (dd, J=8.9 and 2.5 Hz, 1H); 3.96 (s, 3H); 3.52-3.44 (m, 2H); 3.23-3.18 (m, 2H); 1.94 (s, 3H).

$^{13}$C NMR spectroscopic analysis (CD$_3$OD, 75.5 MHz, δ in ppm): 173.4 (s); 159.4 (s); 135.1 (s); 134.6 (s); 131.2 (d); 130.8 (s); 128.2 (d); 127.9 (d); 124.2 (d); 119.3 (d); 103.2 (d); 55.9 (q); 41.4 (t); 34.2 (t); 22.6 (q).

EXAMPLE 7

N-[2-(7-methoxynaphthalen-1-yl)ethyl]acetamide

Step A:
1-(2-hydroxyethyl)-7-methoxynaphthalen-2-yl 4-methylbenzenesulphonate

To a solution of the product obtained in Step A of Example 4 (109 mg; 0.5 mmol) in tetrahydrofuran (2.5 mL) there are added at 0° C. potassium tert-butoxide (56.4 mg; 0.5 mmol) and then, after 5 minutes, tosyl chloride (95 mg; 0.5 mmol). After stirring for 3 hours, the solution is allowed to return to ambient temperature and is stirred for 15 hours more. The solvent is evaporated off and the crude product obtained is purified by chromatography on a silica gel column (eluant: ethyl acetate/petroleum ether 50/50) to yield a mixture of two diastereoisomers (116 mg; 62%) in a ratio of 88:12. The mixture is used as such without any other purification.

$^1$H NMR spectroscopic analysis (CDCl$_3$, 300.13 MHz, δ in ppm): 7.83 (d, J=8.2 Hz, 2H); 7.71 (d, J=9.1 Hz, 1H); 7.59 (d, J=8.9 Hz, 1H); 7.35 (d, J=8.2 Hz, 2H); 7.29 (d, J=2.4 Hz, 1H); 7.15 (dd, J=8.9 and 2.4 Hz, 1H); 7.04 (d, J=9.1 Hz, 1H); 3.91 (s, 3H); 3.87 (t, J=7.1 Hz, 2H); 3.23 (t, J=7.1 Hz, 2H); 2.46 (s, 3H).

$^{13}$C NMR spectroscopic analysis (CDCl$_3$, 75.5 MHz, δ in ppm): 158.6 (s); 146.7 (s); 145.7 (s); 134.5 (s); 133.3 (s); 130.3 (d); 130.1 (2×d); 128.5 (2×d); 128.2 (d); 127.8 (s); 125.7 (s); 118.5 (d); 118.3 (d); 103.4 (d); 62.1 (t); 55.5 (q); 29.7 (t); 21.9 (q).

Step B: 2-(7-methoxynaphthalen-1-yl)ethanol

The mixture of diastereoisomers obtained in Step A above (80 mg; 0.176 mmol of the appropriate isomer), nickel chloride hexahydrate (51 mg; 0.215 mmol), dichloromethane (2 mL) and methanol (2 mL) are introduced into a sealed flask. Argon is then bubbled into the solution for 5 minutes, and then sodium borohydride (146 mg; 4.3 mmol) is added in small portions with caution. After stirring for one hour at ambient temperature under argon, dilute aqueous HCl solution is added. After stirring for 4 hours, the mixture is filtered over Celite and washed with ethanol. The solvent is evaporated off and the crude product obtained is purified by chromatography on a silica gel column (eluant: ethyl acetate/petroleum ether 40/60) to yield the title product (22 mg; 62%).

$^1$H NMR spectroscopic analysis (CDCl$_3$, 300.13 MHz, δ in ppm): 7.72 (d, J=9.1 Hz, 1H); 7.63 (d, J=8.1 Hz, 1H); 7.3-7.21 (m, 3H); 7.13 (dd, J=9.1 and 2.6 Hz, 1H); 3.93 (t, J=6.7 Hz, 2H); 3.88 (s, 3H); 3.24 (d, J=6.7 Hz, 2H); 1.99 (bs, 1H).

$^{13}$C NMR spectroscopic analysis (CDCl$_3$, 75.5 MHz, δ in ppm): 157.8 (s); 133.2 (s); 133.0 (s); 130.4 (d); 129.4 (s); 127.7 (d); 127.1 (d); 123.3 (d); 118.1 (d); 102.5 (d); 62.7 (t); 55.4 (q); 36.4 (t).

Mass spectrometry (ESI; m/z (%)): 202 (29) [M]$^{+}$; 171 (100).

Step C: 2-(7-methoxynaphthalen-1-yl)ethyl methanesulphonate

To a solution of the product of Step B above (275 mg; 1.361 mmol) in dichloromethane (7 mL) there are added at 0° C. triethylamine (227 μL; 1.633 mmol) and mesylsulphonyl chloride (116 μL; 1.498 mmol). After stirring for one hour, the solvents are evaporated off and the residue is taken up in diethyl ether and water. After separation, the organic phase is washed three times with water and with brine, dried over sodium sulphate and filtered. Evaporating off the solvent yields the clean expected product without any other additional purification (356 mg; 93%).

$^1$H NMR spectroscopic analysis (CDCl$_3$, 300.13 MHz, δ in ppm): 7.72 (d, J=9.1 Hz, 1H); 7.66 (d, J=8.9 Hz, 1H); 7.31-7.21 (m, 3H); 7.13 (dd, J=9.1 and 2.5 Hz, 1H); 4.47 (t, J=7.4 Hz, 2H); 3.92 (s, 3H); 3.45 (d, J=7.4 Hz, 2H); 2.77 (s, 3H).

¹³C NMR spectroscopic analysis (CDCl₃, 75.5 MHz, δ in ppm): 158.2 (s); 133.0 (s); 133.0 (s); 130.6 (s); 130.4 (d); 129.3 (s); 128.0 (d); 127.7 (d); 123.2 (d); 118.4 (d); 101.9 (d); 67.9 (t); 55.5 (q); 37.4 (q); 33.3 (t).

Step D:
N-[2-(7-methoxynaphthalen-1-yl)ethyl]acetamide

The product of Step C above (356 mg; 1.271 mmol), acetonitrile (7 mL) and aqueous 35% ammonia solution (5 mL) are introduced into a flask. The flask is placed in a bath heated to 110° C. and the solution is stirred for 3 hours. The solution is diluted with ethyl acetate and washed with aqueous 2M sodium hydroxide solution, water and brine, and then dried over sodium sulphate and filtered. After evaporating off the solvent, the crude product is dissolved in acetic anhydride (2 mL) in the presence of sodium acetate (500 mg). After stirring for one hour, water and ethyl acetate are added and, after stirring for 15 minutes, the organic phase is washed twice with aqueous 2M sodium hydroxide solution, washed with water and brine, dried over sodium sulphate and filtered. The solvent is evaporated off and the crude product obtained is then purified by chromatography on a silica gel column (eluant: ethyl acetate) to yield the title product (230 mg; 74%).

¹H NMR spectroscopic analysis (CD₃OD, 300.13 MHz, δ in ppm): 8.21 (bs, 1H); 7.74 (d, J=8.9 Hz, 1H); 7.65 (d, J=8.0 Hz, 1H); 7.52 (d, J=2.5 Hz, 1H); 7.31-7.2 (m, 2H); 7.11 (dd, J=8.9 and 2.5 Hz, 1H); 3.96 (s, 3H); 3.52-3.44 (m, 2H); 3.23-3.18 (m, 2H); 1.94 (s, 3H).

¹³C NMR spectroscopic analysis (CD₃OD, 75.5 MHz, δ in ppm): 173.4 (s); 159.4 (s); 135.1 (s); 134.6 (s); 131.2 (d); 130.8 (s); 128.2 (d); 127.9 (d); 124.2 (d); 119.3 (d); 103.2 (d); 55.9 (q); 41.4 (t); 34.2 (t); 22.6 (q).

EXAMPLE 8

N-[2-(7-methoxynaphthalen-1-yl)ethyl]acetamide

Step A:
2-(2-hydroxy-7-methoxynaphthalen-1-yl)acetamide 7N methanolic ammonia solution (10 mL; 70 mmol) and the product obtained in Step A of Example 3 (1.5 g; 7 mmol) are introduced into a sealed flask. After stirring for 18 hours at 100° C., the solvent is evaporated off to yield the crude title product (1.58 g; 98%), which is used directly without any other additional purification.

¹H NMR spectroscopic analysis (DMSO-d₆, 300.13 MHz, δ in ppm): 9.87 (bs, 1H); 7.68 (d, J=9.0 Hz, 1H); 7.59 (d, J=8.7 Hz, 1H); 7.36 (bs, 1H); 7.18 (d, J=2.4 Hz, 1H); 7.01 (d, J=8.7 Hz, 1H); 7.01 (bs, 1H); 6.94 (dd, J=9.0 and 2.4 Hz, 1H); 3.84 (s, 3H); 3.79 (s, 2H).

Step B:
1-[2-(acetylamino)ethyl]-7-methoxynaphthalen-2-yl acetate

Lithium aluminium hydride (396 mg; 10.432 mmol) is added to a suspension of the product of Step A above (1.205 g; 5.216 mmol) in tetrahydrofuran (25 mL). After stirring at reflux for 8 hours, the mixture is cooled to 0° C. and water (40 mL) and then citric acid (10 g) are added. After stirring for 14 hours, the mixture is neutralised using saturated aqueous NaHCO₃ solution and the product is extracted three times with ethyl acetate. The organic phases are combined, washed with water and with brine, and then dried over sodium sulphate and filtered. After evaporation, the crude product (802 mg) is dissolved in acetic anhydride (3 mL) in the presence of sodium acetate (500 mg). The mixture is stirred for 16 hours and is then poured into dilute aqueous NaHCO₃ solution. The product is extracted three times with ethyl acetate and the organic phases are combined, washed with water and with brine, dried over sodium sulphate and filtered. After evaporating off the solvents, the crude product is purified by chromatography on a silica gel column (eluant: ethyl acetate/methanol, gradient from 100/0 to 95/5) to yield the title product in the form of a white solid (337 mg; 21%).

Melting point: 149-151° C.

¹H NMR spectroscopic analysis (CDCl₃, 300.13 MHz, δ in ppm): 7.73 (d, J=8.9 Hz, 1H); 7.68 (d, J=8.8 Hz, 1H); 7.42 (d, J=2.2 Hz, 1H); 7.14 (dd, J=8.8 and 2.2 Hz, 1H); 7.01 (d, J=8.9 Hz, 1H); 5.75 (bs, 1H); 3.97 (s, 3H); 3.52 (m, 2H); 3.19 (t, J=6.7 Hz, 2H); 2.39 (s, 3H); 1.9 (s, 3H).

¹³C NMR spectroscopic analysis (CDCl₃, 75.5 MHz, δ in ppm): 170.7 (s); 170.6 (s); 158.6 (s); 147.5 (s); 134.3 (s); 130.3 (d); 128.2 (d); 127.5 (s); 124.1 (s); 119.0 (d); 118.2 (d); 102.9 (d); 55.6 (q); 39.1 (t); 25.9 (t); 23.4 (q); 21.1 (q).

Step C:
1-[2-(acetylamino)ethyl]-7-methoxynaphthalen-2-yl 4-methylbenzenesulphonate The product of Step B above (230 mg; 0.764 mmol) is added to a solution of sodium hydroxide (61 mg; 1.528 mmol) in absolute ethanol (10 mL). After stirring for one hour, the solvent is evaporated off. The residue is taken up in a mixture of ethyl acetate/dilute aqueous hydrochloric acid solution. After separation, the organic phase is washed with water and with brine, then dried over sodium sulphate and filtered. After evaporating off the solvent, the crude product is dissolved in dichloromethane (4 mL) in the presence of triethylamine (150 μL; 2.47 mmol) and tosyl chloride (174 mg; 0.917 mmol). After stirring for 16 hours at ambient temperature, the solvent is evaporated off. The residue is taken up in ethyl acetate and water. After separation, the organic phase is washed with water and with brine, dried over sodium sulphate and filtered. After evaporating off the solvent, the crude product is purified by chromatography on a silica gel column (eluant: ethyl acetate) to yield the title product (261 mg; 83%).

¹H NMR spectroscopic analysis (CDCl₃, 300.13 MHz, δ in ppm): 7.81 (d, J=8.2 Hz, 2H); 7.68 (d, J=8.9 Hz, 1H); 7.62 (d, J=2.4 Hz, 1H); 7.55 (d, J=8.9 Hz, 1H); 7.36 (d, J=8.2 Hz, 2H); 7.14 (dd, J=8.9 and 2.4 Hz, 1H); 6.89 (d, 8.9 Hz, 1H); 5.97 (m, 1H); 4.01 (s, 3H); 3.53-3.46 (m, 2H); 3.22-3.17 (m, 2H); 2.46 (s, 3H); 1.95 (s, 3H).

¹³C NMR spectroscopic analysis (CDCl₃, 75.5 MHz, δ in ppm): 170.9 (s); 158.9 (s); 146.4 (s); 145.7 (s); 134.6 (s); 133.3 (s); 130.1 (2×d); 130.0 (d); 128.5 (2×d); 128.2 (d); 127.7 (s); 126.2 (s); 119.2 (d); 117.8 (d); 103.3 (d); 55.8 (q); 39.4 (t); 26.4 (t); 23.4 (q); 21.9 (q).

Step D:
N-[2-(7-methoxynaphthalen-1-yl)ethyl]acetamide

The title product is obtained according to the process described in Step D of Example 2, using the product of Step C above as starting reagent.

¹H NMR spectroscopic analysis (CD₃OD, 300.13 MHz, δ in ppm): 8.21 (bs, 1H); 7.74 (d, J=8.9 Hz, 1H); 7.65 (d, J=8.0 Hz, 1H); 7.52 (d, J=2.5 Hz, 1H); 7.31-7.2 (m, 2H); 7.11 (dd, J=8.9 and 2.5 Hz, 1H); 3.96 (s, 3H); 3.52-3.44 (m, 2H); 3.23-3.18 (m, 2H); 1.94 (s, 3H).

¹³C NMR spectroscopic analysis (CD₃OD, 75.5 MHz, δ in ppm): 173.4 (s); 159.4 (s); 135.1 (s); 134.6 (s); 131.2 (d); 130.8 (s); 128.2 (d); 127.9 (d); 124.2 (d); 119.3 (d); 103.2 (d); 55.9 (q); 41.4 (t); 34.2 (t); 22.6 (q).

EXAMPLE 9

N-[2-(7-methoxynaphthalen-1-yl)ethyl]acetamide

Step A: 1-(2-amino-2-oxoethyl)-7-methoxynaphthalen-2-yl 4-methylbenzenesulphonate Sodium hydride (60% in mineral oil; 78 mg; 1.953 mmol) is added at 0° C. to a solution of the product obtained in Step A of Example 8 (376 mg; 1.628 mmol) in dimethylformamide (3 mL). After stirring for 30 minutes, tosyl chloride (341 mg; 1.79 mmol) is introduced in one portion. After stirring for 2 hours, the reaction mixture is diluted with ethyl acetate and then washed twice with water and twice with brine. The organic phase is dried over sodium sulphate and filtered. After evaporating off the solvents, the crude product is purified by chromatography on a silica gel column (eluant: ethyl acetate/dichloromethane 30/70) to yield the title product in the form of a white solid (260 mg; 40%).

¹H NMR spectroscopic analysis (CDCl₃, 300.13 MHz, δ in ppm): 7.89 (d, J=7.9 Hz, 2H); 7.72 (d, J=9.0 Hz, 1H); 7.66 (d, J=9.0 Hz, 1H); 7.4 (d, J=7.9 Hz, 2H); 7.37 (d, J=2.4 Hz, 1H); 7.17 (dd, J=9.0 and 2.4 Hz, 1H); 7.01 (d, J=9.0 Hz, 1H); 6.02 (bs, 1H); 5.48 (bs, 1H); 3.93 (s, 2H); 3.91 (s, 3H); 2.50 (s, 3H).

Step B: 2-(7-methoxynaphthalen-1-yl)acetamide

The product obtained in Step A above (50 mg; 0.13 mmol), nickel chloride hexahydrate (31 mg; 0.13 mmol), dichloromethane (1.3 mL) and methanol (1.3 mL) are introduced into a sealed flask. Argon is then bubbled into the solution for 5 minutes and then sodium borohydride (88 mg; 2.6 mmol) is added in small portions with caution. After stirring for 1 hour under argon at ambient temperature, water is added. After stirring for 15 minutes, the mixture is filtered over Celite and then washed with dichloromethane and ethyl acetate. The organic fraction is dried over sodium sulphate and then filtered. After evaporating off the solvents, the crude product is purified by chromatography on a silica gel column (eluant: ethyl acetate) to yield the title product (8 mg; 29%).

¹H NMR spectroscopic analysis (DMSO-d₆, 300.13 MHz, δ in ppm): 7.84 (d, J=9.0 Hz, 1H); 7.73 (d, J=8.0 Hz, 1H); 7.62 (bs, 1H); 7.41-7.36 (m, 2H); 7.28 (dd, J=8.0 and 7.1 Hz, 1H); 7.18 (dd, J=9.0 and 2.4 Hz, 1H); 7.02 (bs, 1H); 3.88 (s, 3H); 3.82 (s, 2H).

¹³C NMR spectroscopic analysis (DMSO-d₆, 75.5 MHz, δ in ppm): 172.3 (s); 157.3 (s); 133.2 (s); 131.8 (s); 130.0 (d); 128.7 (s); 128.4 (d); 126.7 (d); 123.1 (d); 117.7 (d); 103.4 (d); 55.2 (q); 40.2 (t).

Step C: (7-methoxynaphthalen-1-yl)acetonitrile

The title product is obtained according to the protocol described in Step F of Preparation 1 of patent specification EP 0 447 285 using the product of Step B above as starting reagent.

Melting point: 86-87° C.

¹H NMR spectroscopic analysis (CDCl₃, 300.13 MHz, δ in ppm): 7.78 (d, J=8.9 Hz, 1H); 7.77 (d, J=7.8 Hz, 1H); 7.52 (d, J=7.1 Hz, 1H); 7.32 (dd, J=7.8 and 7.1 Hz, 1H); 7.21 (dd, J=8.9 and 2.4 Hz, 1H); 7.03 (d, J=2.4 Hz, 1H); 4.0 (s, 2H); 3.94 (s, 3H).

¹³C NMR spectroscopic analysis (CDCl₃, 75.5 MHz, δ in ppm): 158.5 (s); 132.0 (s); 130.6 (d); 129.1 (s); 128.8 (d); 127.1 (d); 124.4 (s); 123.2 (d); 118.8 (d); 117.7 (s); 101.3 (d); 55.4 (q); 21.9 (t).

Step D:
N-[2-(7-methoxynaphthalen-1-yl)ethyl]acetamide

The title product is obtained according to the process described in Step E of Example 1 using the product of Step C above.

Melting point: 108° C.

¹H NMR spectroscopic analysis (CD₃OD, 300.13 MHz, δ in ppm): 8.21 (bs, 1H); 7.74 (d, J=8.9 Hz, 1H); 7.65 (d, J=8.0 Hz, 1H); 7.52 (d, J=2.5 Hz, 1H); 7.31-7.2 (m, 2H); 7.11 (dd, J=8.9 and 2.5 Hz, 1H); 3.96 (s, 3H); 3.52-3.44 (m, 2H); 3.23-3.18 (m, 2H); 1.94 (s, 3H).

¹³C NMR spectroscopic analysis (CD₃OD, 75.5 MHz, δ in ppm): 173.4 (s); 159.4 (s); 135.1 (s); 134.6 (s); 131.2 (d); 130.8 (s); 128.2 (d); 127.9 (d); 124.2 (d); 119.3 (d); 103.2 (d); 55.9 (q); 41.4 (t); 34.2 (t); 22.6 (q).

EXAMPLE 10

N-[2-(7-methoxynaphthalen-1-yl)ethyl]acetamide

Step A:
2-methoxy-7-(prop-2-en-1-yloxy)naphthalene

Allyl bromide (4.4 mL; 50.56 mmol) is added to a solution of 7-methoxy-naphthalen-2-ol (5.865 g; 33.71 mmol) and potassium carbonate (13.96 g; 101.12 mmol) in acetone (33 mL). After stirring at 65° C. for 16 hours, the mixture is cooled to ambient temperature and water (60 mL) is added. After stirring for 3 hours, the product is extracted three times with ethyl acetate. The organic fractions are combined, washed twice with water and then with brine, dried over sodium sulphate and filtered. Evaporating off the solvents yields a crude product (7.963 g) which is used directly in the next Step without further purification.

¹H NMR spectroscopic analysis (CDCl₃, 300.13 MHz, δ in ppm): 7.68 (d, J=8.9 Hz, 1H); 7.67 (d, J=8.9 Hz, 1H); 7.08-6.99 (m, 3H); 6.13 (m, 1H); 5.48 (m, 1H); 5.34 (m, 1H); 4.65 (m, 1H); 3.92 (s, 3H).

Step B: 7-methoxy-1-(prop-2-en-1-yl)naphthalen-2-ol

Using a flask, the product of Step A above (7.963 g; 33.71 mmol) is placed in a bath heated to 200° C. for 2.5 hours. After cooling, the crude product is used directly in the next Step without further purification.

¹H NMR spectroscopic analysis (CDCl₃, 300.13 MHz, δ in ppm): 7.69 (d, J=8.9 Hz, 1H); 7.6 (d, J=8.7 Hz, 1H); 7.2 (d, J=2.4 Hz, 1H); 7.03 (dd, J=8.9 and 2.4 Hz, 1H); 6.95 (d, J=8.7 Hz, 1H); 6.08 (m, 1H); 5.28 (s, 1H); 5.14 (m, 1H); 5.1 (m, 1H); 3.93 (s, 3H); 3.8 (m, 1H).

Step C: 7-methoxy-1-(prop-2-en-1-yl)naphthalen-2-yl 4-methylbenzenesulphonate

Triethylamine (1.95 mL; 14.02 mmol) and tosyl chloride (2.23 g; 11.68 mmol) are added to a solution of the product of Step B above (2.5 g; 11.68 mmol) in dichloromethane (22 mL). After stirring for 16 hours at ambient temperature, the solvent is evaporated off and the residue is taken up in ethyl acetate and water. After separation, the organic phase is washed with water and with brine, dried over sodium sulphate and filtered. After evaporating off the solvent, the crude product is purified by chromatography on a silica gel column (eluant: ethyl acetate/petroleum ether, gradient from 10/90 to 20/80) to yield the title product (3.79 g; 88%).

$^1$H NMR spectroscopic analysis (CDCl$_3$, 300.13 MHz, δ in ppm): 7.8 (d, J=8.3 Hz, 2H); 7.71 (d, J=8.9 Hz, 1H); 7.6 (d, J=8.9 Hz, 1H); 7.33 (d, J=8.3 Hz, 2H); 7.24 (d, J=2.5 Hz, 1H); 7.14 (dd, J=8.9 and 2.5 Hz); 7.1 (d, J=8.9 Hz, 1H); 5.79 (m, 1H); 5.02-4.95 (m, 2H); 3.88 (s, 3H); 3.68 (d, J=5.9 Hz, 2H); 2.46 (s, 3H).

$^{13}$C NMR spectroscopic analysis (CDCl$_3$, 75.5 MHz, δ in ppm): 158.3 (s); 146.1 (s); 145.5 (s); 135.5 (d); 134.4 (s); 133.3 (s); 130.1 (d); 130.0 (2×d); 128.5 (2×d); 128.0 (d); 127.7 (s); 126.6 (s); 118.5 (d); 118.4 (d); 116.1 (t); 103.9 (d); 55.4 (q); 30.5 (t); 21.8 (q).

Step D:
1-(2,3-dihydroxypropyl)-7-methoxynaphthalen-2-yl 4-methylbenzenesulphonate 4-Methylmorpholine N-oxide hydrate (1.666 g; 12.35 mmol) and osmium tetroxide (4% in water; 653 μL, 0.01 mmol) are added to a solution of the product of Step C above (3.786 g; 10.29 mmol) in acetone (40 mL) and deionised water (10 mL). After stirring at ambient temperature for 20 hours, sodium thiosulphate pentahydrate (1 g) is added. After another hour's stirring, the solvents are evaporated off. The residue is taken up in ethyl acetate and the organic phase is washed with brine, dried over sodium sulphate and filtered. After evaporating off the solvent, the crude product is purified by chromatography on a silica gel column (eluant: ethyl acetate) to yield the title product in the form of a white solid (3.617 g; 87%).

$^1$H NMR spectroscopic analysis (CDCl$_3$, 300.13 MHz, δ in ppm): 7.81 (d, J=8.3 Hz, 2H); 7.69 (d, J=9.0 Hz, 1H); 7.58 (d, J=9.0 Hz, 1H); 7.33 (d, J=8.3 Hz, 2H); 7.13 (dd, J=9.0 and 2.4, 1H); 7.02 (d, J=9.0 Hz, 1H); 4.01 (m, 1H); 3.88 (s, 3H); 3.63-3.47 (m, 2H); 3.11 (d, J=7.0 Hz, 2H); 2.9 (bs, 1H); 2.62 (bs, 1H); 2.44 (s, 3H).

$^{13}$C NMR spectroscopic analysis (CDCl$_3$, 75.5 MHz, δ in ppm): 158.6 (s); 146.8 (s); 145.8 (s); 134.6 (s); 133.1 (s); 130.2 (d); 130.1 (2×d); 128.4 (2×d); 128.3 (d); 127.7 (s); 125.4 (s); 118.6 (d); 118.0 (d); 103.6 (d); 72.0 (d); 65.8 (t); 55.5 (q); 30.1 (t); 21.8 (q).

Step E: 7-methoxy-1-(2-oxoethyl)naphthalen-2-yl 4-methylbenzenesulphonate

Sodium periodate (785 mg; 3.671 mmol) and aqueous 2M HCl solution (1.8 mL) are added to a solution of the product of Step D above (1.23 g; 3.06 mmol) in tetrahydrofuran (12 mL) and water (3 mL). After 30 minutes, the mixture is neutralised with dilute aqueous NaHCO$_3$ solution and the product is then extracted with ethyl acetate. The organic fractions are combined, dried over sodium sulphate and filtered. Evaporating off the solvents yields the title product in the form of a clean white solid (1.13 g; 100%), which is used directly in the next Step.

Melting point: 101-103° C.

$^1$H NMR spectroscopic analysis (CDCl$_3$, 300.13 MHz, δ in ppm): 9.43 (t, J=2.6 Hz, 1H); 7.78 (d, J=8.3 Hz, 2H); 7.74 (d, J=8.9 Hz, 1H); 7.68 (d, J=8.9 Hz, 1H); 7.35 (d, J=8.3 Hz, 2H); 7.17 (dd, J=8.9 and 2.4 Hz, 1H); 7.04 (d, J=8.9 Hz, 1H); 6.97 (d, J=2.4 Hz, 1H); 3.98 (d, J=2.6 Hz, 2H); 3.88 (s, 3H); 2.46 (s, 3H).

$^{13}$C NMR spectroscopic analysis (CDCl$_3$, 75.5 MHz, δ in ppm): 199.2 (d); 159.1 (s); 146.8 (s); 146.0 (s); 134.7 (s); 132.7 (s); 130.4 (d); 130.2 (2×d); 129.4 (s); 128.6 (2×d); 127.6 (s); 120.1 (s); 119.1 (d); 118.6 (d); 102.9 (d); 55.5 (q); 41.7 (t); 21.9 (q).

Step F: 2-(7-methoxynaphthalen-1-yl)ethanol

To a solution of the product of Step E above (950 mg; 2.567 mmol) in methanol (13 mL) there are added, under argon, nickel chloride (366 mg; 2.824 mmol) and sodium borohydride (1.3 g; 38.2 mmol) in small portions. After stirring for one hour, the mixture is hydrolysed with aqueous 2M HCl solution (80 mL) and is then stirred for 30 minutes in the presence of ethyl acetate. The heterogeneous solution is filtered over Celite and washed with ethyl acetate. The two phases are separated and the organic fraction is washed with brine, dried over sodium sulphate and filtered. After evaporating off the solvent, the crude product is purified by chromatography on a silica gel column (eluant: ethyl acetate/petroleum ether 40/60) to yield the title product in the form of a white solid (442 mg; 85%).

$^1$H NMR spectroscopic analysis (CDCl$_3$, 300.13 MHz, δ in ppm): 7.72 (d, J=9.1 Hz, 1H); 7.63 (d, J=8.1 Hz, 1H); 7.3-7.21 (m, 3H); 7.13 (dd, J=9.1 and 2.6 Hz, 1H); 3.93 (t, J=6.7 Hz, 2H); 3.88 (s, 3H); 3.24 (d, J=6.7 Hz, 2H); 1.99 (bs, 1H).

$^{13}$C NMR spectroscopic analysis (CDCl$_3$, 75.5 MHz, δ in ppm): 157.8 (s); 133.2 (s); 133.0 (s); 130.4 (d); 129.4 (s); 127.7 (d); 127.1 (d); 123.3 (d); 118.1 (d); 102.5 (d); 62.7 (t); 55.4 (q); 36.4 (t).

Mass spectrometry (ESI; m/z (%)): 202 (29) [M]+'; 171 (100).

Step G: 2-(7-methoxynaphthalen-1-yl)ethyl methanesulphonate

The title product is obtained according to the process described in Step C of Example 7, using the product of Step F above as starting reagent.

$^1$H NMR spectroscopic analysis (CDCl$_3$, 300.13 MHz, δ in ppm): 7.72 (d, J=9.1 Hz, 1H); 7.66 (d, J=8.9 Hz, 1H); 7.31-7.21 (m, 3H); 7.13 (dd, J=9.1 and 2.5 Hz, 1H); 4.47 (t, J=7.4 Hz, 2H); 3.92 (s, 3H); 3.45 (d, J=7.4 Hz, 2H); 2.77 (s, 3H).

$^{13}$C NMR spectroscopic analysis (CDCl$_3$, 75.5 MHz, δ in ppm): 158.2 (s); 133.0 (s); 133.0 (s); 130.6 (d); 130.4 (d); 129.3 (s); 128.0 (d); 127.7 (d); 123.2 (d); 118.4 (d); 101.9 (d); 67.9 (t); 55.5 (q); 37.4 (q); 33.3 (t).

Step H:
N-[2-(7-methoxynaphthalen-1-yl)ethyl]acetamide

The title product is obtained according to the process described in Step D of Example 7, using the product of Step G above as starting reagent.

$^1$H NMR spectroscopic analysis (CD$_3$OD, 300.13 MHz, δ in ppm): 8.21 (bs, 1H); 7.74 (d, J=8.9 Hz, 1H); 7.65 (d, J=8.0 Hz, 1H); 7.52 (d, J=2.5 Hz, 1H); 7.31-7.2 (m, 2H); 7.11 (dd, J=8.9 and 2.5 Hz, 1H); 3.96 (s, 3H); 3.52-3.44 (m, 2H); 3.23-3.18 (m, 2H); 1.94 (s, 3H).

$^{13}$C NMR spectroscopic analysis (CD$_3$OD, 75.5 MHz, δ in ppm): 173.4 (s); 159.4 (s); 135.1 (s); 134.6 (s); 131.2 (d);

130.8 (s); 128.2 (d); 127.9 (d); 124.2 (d); 119.3 (d); 103.2 (d); 55.9 (q); 41.4 (t); 34.2 (t); 22.6 (q).

EXAMPLE 11

N-[2-(7-methoxynaphthalen-1-yl)ethyl]acetamide

Step A:
3-(7-methoxynaphthalen-1-yl)propane-1,2-diol

The product obtained in Step D of Example 10 (44 mg; 0.11 mmol), nickel chloride (16 mg; 0.12 mmol) and methanol (1 mL) are introduced, under argon, into a sealed flask. Sodium borohydride (74 mg; 2.19 mmol) is then added in small portions with caution. After stirring for 2 hours, water (1 mL) and then hydrogen peroxide (35% in water; 1 mL) are added and the mixture is stirred for 2 hours. Brine is then added and the aqueous phase is extracted three times with ethyl acetate. The organic phases are combined, dried over sodium sulphate and filtered. Evaporating off the solvents yields a clean product (22 mg; 86%) without needing additional purification.

$^1$H NMR spectroscopic analysis (CDCl$_3$, 300.13 MHz, δ in ppm): 7.75 (d, J=9.1 Hz, 1H); 7.68 (d, J=8.1 Hz, 1H); 7.32-7.23 (m, 3H); 7.16 (dd, J=9.1 and 2.4 Hz, 1H); 4.11 (m, 1H); 3.92 (s, 3H); 3.72-3.55 (m, 2H); 3.25-3.1 (m, 2H); 2.54 (bs, 2H, OH).

Step B: (7-methoxynaphthalen-1-yl)acetaldehyde

The title product is obtained according to the process described in Step E of Example 10, using the product of Step A above instead of 1-(2,3-dihydroxypropyl)-7-methoxynaphthalen-2-yl 4-methylbenzenesulphonate.

$^1$H NMR spectroscopic analysis (CDCl$_3$, 300.13 MHz, δ in ppm): 9.74 (t, J=2.6 Hz, 1H); 7.74-7.84 (m, 2H); 7.38 (d, J=6.0 Hz, 1H); 7.32 (t, J=7.5 Hz, 1H); 7.19 (dd, J=9.0 Hz and 2.4 Hz, 1H); 7.1 (d, J=2.4 Hz, 1H); 4.05 (d, J=2.6 Hz, 2H); 3.92 (s, 3H).

$^{13}$C NMR spectroscopic analysis (CDCl$_3$, 75.5 MHz, δ in ppm): 199.85; 158.29; 133.54; 130.44; 129.32; 129.07; 128.23; 126.83; 123.36; 118.63; 102.12; 55.36; 48.83.

Step C: 2-(7-methoxynaphthalen-1-yl)ethanol

Sodium borohydride (38 mg; 1 mmol) is added to a solution of the product of Step B above (20 mg; 0.1 mmol) in ethanol (1 mL). After stirring for 2 hours at ambient temperature, the mixture is hydrolysed with 2M aqueous HCl solution (2 mL) and is then stirred for 30 minutes in the presence of ethyl acetate (1 mL). The solution is extracted 4 times with ethyl acetate. The organic fractions are combined, dried over sodium sulphate and filtered. After evaporating off the solvent, the crude product is purified by chromatography on a silica gel column (eluant: ethyl acetate/petroleum ether 20/80) to yield the title product in the form of a white solid (19.8 mg; 98%).

$^1$H NMR spectroscopic analysis (CDCl$_3$, 300.13 MHz, δ in ppm): 7.72 (d, J=9.1 Hz, 1H); 7.63 (d, J=8.1 Hz, 1H); 7.3-7.21 (m, 3H); 7.13 (dd, J=9.1 and 2.6 Hz, 1H); 3.93 (t, J=6.7 Hz, 2H); 3.88 (s, 3H); 3.24 (d, J=6.7 Hz, 2H); 1.99 (bs, 1H).

$^{13}$C NMR spectroscopic analysis (CDCl$_3$, 75.5 MHz, δ in ppm): 157.8 (s); 133.2 (s); 133.0 (s); 130.4 (s); 129.4 (s); 127.7 (d); 127.1 (d); 123.3 (d); 118.1 (d); 102.5 (d); 62.7 (t); 55.4 (q); 36.4 (t).

Mass spectrometry (ESI; m/z (%)): 202 (29) [M]$^{+}$; 171 (100).

Step D: 2-(7-methoxynaphthalen-1-yl)ethyl methanesulphonate

The title product is obtained according to the process described in Step C of Example 7 using the product of Step C above as starting reagent.

$^1$H NMR spectroscopic analysis (CDCl$_3$, 300.13 MHz, δ in ppm): 7.72 (d, J=9.1 Hz, 1H); 7.66 (d, J=8.9 Hz, 1H); 7.31-7.21 (m, 3H); 7.13 (dd, J=9.1 and 2.5 Hz, 1H); 4.47 (t, J=7.4 Hz, 2H); 3.92 (s, 3H); 3.45 (d, J=7.4 Hz, 2H); 2.77 (s, 3H).

$^{13}$C NMR spectroscopic analysis (CDCl$_3$, 75.5 MHz, δ in ppm): 158.2 (s); 133.0 (s); 133.0 (s); 130.6 (s); 130.4 (d); 129.3 (s); 128.0 (d); 127.7 (d); 123.2 (d); 118.4 (d); 101.9 (d); 67.9 (t); 55.5 (q); 37.4 (q); 33.3 (t).

Step E:
N-[2-(7-methoxynaphthalen-1-yl)ethyl]acetamide

The title product is obtained according to the process described in Step D of Example 7 using the product of Step D above as starting reagent.

$^1$H NMR spectroscopic analysis (CD$_3$OD, 300.13 MHz, δ in ppm): 8.21 (bs, 1H); 7.74 (d, J=8.9 Hz, 1H); 7.65 (d, J=8.0 Hz, 1H); 7.52 (d, J=2.5 Hz, 1H); 7.31-7.2 (m, 2H); 7.11 (dd, J=8.9 and 2.5 Hz, 1H); 3.96 (s, 3H); 3.52-3.44 (m, 2H); 3.23-3.18 (m, 2H); 1.94 (s, 3H).

$^{13}$C NMR spectroscopic analysis (CD$_3$OD, 75.5 MHz, δ in ppm): 173.4 (s); 159.4 (s); 135.1 (s); 134.6 (s); 131.2 (d); 130.8 (s); 128.2 (d); 127.9 (d); 124.2 (d); 119.3 (d); 103.2 (d); 55.9 (q); 41.4 (t); 34.2 (t); 22.6 (q).

The invention claimed is:

1. A process for the industrial synthesis of a compound of formula (I):

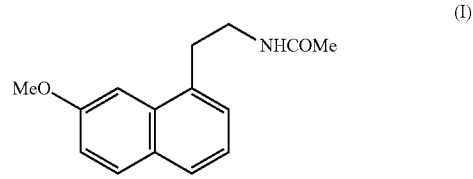

wherein 7-methoxy-naphthalen-2-ol of formula (II):

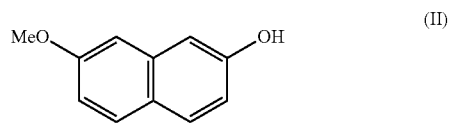 [SMILES: COc1ccc2ccc(O)cc2c1]

is used for reaction, and wherein the group —CH$_2$—X, wherein X represents —N(CH$_3$)$_2$, —CO—N(CH$_2$-Ph)$_2$, —CH$_2$—OH, —CH=CH$_2$ or —CO—NH$_2$, is introduced at position 1 of the compound of formula (II)

to yield a compound of formula

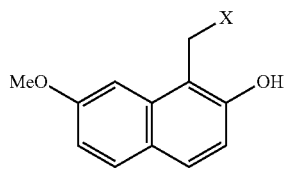
(III)

wherein X represents —N(CH$_3$)$_2$, —CO—N(CH$_2$-Ph)$_2$, —CH$_2$—OH, —CH=CH$_2$ or —CO—NH$_2$;

which compound of formula (III) is subjected to a sulphonylation reaction at the aromatic alcohol and the substituent X of which compound of formula (III) is modified, before or after the aromatic alcohol sulphonylation step, by means of customary chemical reactions to yield a compound of formula (IV):

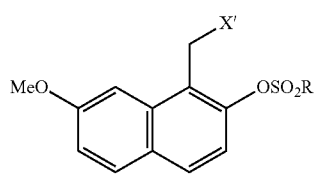
(IV)

wherein X' represents —CN, —CO—NH$_2$, —CH$_2$—OH, —CHO, —CH$_2$—N(CH$_2$-Ph)$_2$, —CH$_2$—NH—CO—CH$_3$, —CH(OH)—CH$_2$—OH or (2,5-dioxopyrrolidin-1-yl)methyl and R represents —CH$_3$, —(CH$_2$)$_2$—CH$_3$, —CF$_3$ or tolyl;

which compound of formula (IV) undergoes a deoxygenation reaction in the presence of a transition metal and a reducing agent to yield:
either, when X' represents the group —CH$_2$—NH—CO—CH$_3$, the compound of formula (I) directly, which is isolated in the form of a solid;
or the compound of formula (V):

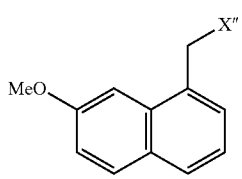
(V)

wherein X" represents —CN, —CH$_2$—N(CH$_2$-Ph)$_2$, —CH$_2$—OH, —CH(OH)—CH$_2$—OH, —CO—NH$_2$, or (2,5-dioxopyrrolidin-1-yl)methyl;

which compound of formula (V) is subjected to customary chemical reactions to yield the compound of formula (I), which is isolated in the form of a solid.

2. The process according to claim 1, wherein the conversion of the compound of formula (II) into the compound of formula (III) is accomplished by means of the action of formaldehyde and dimethylamine to yield the compound of formula (III) wherein X represents —N(CH$_3$)$_2$.

3. The process according to claim 1, wherein the conversion of the compound of formula (II) into the compound of formula (III) is accomplished by means of the action of glyoxal followed by the action of a reducing agent to yield the compound of formula (III) wherein X represents —CH$_2$—OH.

4. The process according to claim 1, wherein the conversion of the compound of formula (II) into the compound of formula (III) is accomplished by means of the action of glyoxal followed by the action of the compound of formula NHR'R wherein R' represents H or a —CH$_2$-Ph group to yield the compound of formula (III) wherein X represents —CO—NH$_2$ or —CO—N(CH$_2$-Ph)$_2$.

5. The process according to claim 1, wherein the conversion of the compound of formula (II) into the compound of formula (III) is accomplished by means of the action of allyl bromide followed by a thermal rearrangement to yield the compound of formula (III) wherein X represents —CH=CH$_2$.

6. The process according to claim 1, wherein, in the conversion of the compound of formula (III) into the compound of formula (IV), the sulphonylation step is accomplished by means of the action of a sulphonyl chloride, a sulphonic anhydride or a sulphonimide.

7. The process according to claim 1, wherein the conversion of the compound of formula (III) into the compound of formula (IV) consists of a step of sulphonylation of the aromatic alcohol followed by modification of the group X by means of customary chemical reactions, X being as defined for formula (III).

8. The process according to claim 1, wherein the conversion of the compound of formula (III) into the compound of formula (IV) consists of modification of the group X by means of customary chemical reactions followed by a step of sulphonylation of the aromatic alcohol, X being as defined for formula (III).

9. The process according to claim 1, wherein the conversion of the compound of formula (IV) into the compound of formula (V) is accomplished in the presence of nickel and a hydride.

10. The process according to claim 1, wherein the conversion of the compound of formula (IV) into the compound of formula (V) is accomplished in the presence of palladium and dihydrogen.

11. The process according to claim 1, wherein the conversion of the compound of formula (IV) into the compound of formula (V) is accomplished in the presence of palladium and an alkaline earth metal.

12. The process according to claim 1, wherein the conversion of the compound of formula (IV) wherein X' represents —CH$_2$—NH—CO—CH$_3$ into the compound of formula (I) is accomplished in the presence of nickel and a hydride.

13. The process according to claim 1, wherein the conversion of the compound of formula (IV) wherein X' represents —CH$_2$—NH—CO—CH$_3$ into the compound of formula (I) is accomplished in the presence of palladium and dihydrogen.

14. The process according to claim 1, wherein the conversion of the compound of formula (IV) wherein X represents —CH$_2$—NH—CO—CH$_3$ into the compound of formula (I) is accomplished in the presence of palladium and an alkaline earth metal.

* * * * *